US007568486B2

(12) United States Patent
Vrus

(10) Patent No.: US 7,568,486 B2
(45) Date of Patent: Aug. 4, 2009

(54) DEVICE FOR THE PRECISE DYEING OF INDIVIDUAL HAIRS AND FOR DYEING HAIR TUFTS WITH PROTECTIVE MECHANISM FOR PROTECTING UNDYED HAIR

(76) Inventor: Iris Vrus, Laniste 5, Zagreb, Croatia (HR) 10020

( * ) Notice: Subject to any disclaimer, the term of this patent is extended or adjusted under 35 U.S.C. 154(b) by 706 days.

(21) Appl. No.: 11/249,089

(22) Filed: Oct. 12, 2005

(65) Prior Publication Data

US 2006/0071024 A1 Apr. 6, 2006

(51) Int. Cl.
*A61K 8/18* (2006.01)
*A45D 24/22* (2006.01)

(52) U.S. Cl. ....................................... 132/208; 132/112

(58) Field of Classification Search ......... 132/108–116, 132/208; 222/137, 145.5, 145.6; 401/44, 401/47
See application file for complete search history.

(56) References Cited

U.S. PATENT DOCUMENTS 3,390,814 A * 7/1968 Creighton, Jr., et al. ..... 222/137
3,570,719 A * 3/1971 Schiff .......................... 222/137
3,587,982 A * 6/1971 Campbell .................... 241/62
6,135,631 A * 10/2000 Keller ........................ 366/339
6,530,685 B1 * 3/2003 Muhlbauer et al. .......... 366/336
6,655,551 B2 * 12/2003 Manne .................... 222/145.6
6,698,622 B2 * 3/2004 Sawhney et al. ............ 222/137
6,729,501 B2 5/2004 Peterson
6,854,621 B2 * 2/2005 Keller ........................ 222/137
2003/0183653 A1 * 10/2003 Bills .......................... 222/137
2004/0194796 A1 * 10/2004 Burghaus .................... 132/108
2004/0251275 A1 * 12/2004 Sams et al. .............. 222/145.6
2006/0272109 A1 * 12/2006 Stern et al. ...................... 8/406

* cited by examiner

*Primary Examiner*—Robyn Doan
(74) *Attorney, Agent, or Firm*—Eric Hanscom; Todd Langford

(57) ABSTRACT

This invention provides several iterations for dyeing individual hairs or hair tufts, and comprises a body with a dye cavity in which one or more dye partitions can be filled, where dye materials are pressed out through screw drive or compression means, and where the dye materials are protected from air until extruded, such that unused portions can be stored rather than thrown away. In a preferred embodiment the dye cavity contains dye partitions for dye material and developer, which are forced by pressure into a mixing spiral which mixes them together and applies the active mixture to a person's hair through either a top attachment or pincers, both of which are constructed of spongy material which soaks up the dye mixture from the mixing spiral. The invention also provides a latex tube which prophylactically isolates the dyed hair such that the dye does not spread in an undesired manner.

33 Claims, 14 Drawing Sheets

DEVICE FOR THE PRECISE DYEING OF INDIVIDUAL HAIRS AND FOR DYEING HAIR TUFTS WITH PROTECTIVE MECHANISM FOR PROTECTING UNDYED HAIR

CROSS REFERENCE TO RELATED APPLICATIONS

This application claims priority from International Application No. WO 2005/032300, PCT/HR 2004/000031, dated Oct. 1, 2004.

STATEMENT REGARDING FEDERALLY SPONSORED RESEARCH OR DEVELOPMENT

This invention was not federally sponsored.

BACKGROUND OF THE INVENTION

This invention provides several iterations for dyeing individual hairs or hair tufts, and comprises a body with a dye cavity in which one or more dye partitions can be filled, where dye materials are pressed out through screw drive or compression means, and where the dye materials are protected from air until extruded, such that unused portions can be stored rather than thrown away. In a preferred embodiment the dye cavity contains dye partitions for dye material and developer, which are forced by pressure into a mixing spiral which mixes them together and applies the active mixture to a person's hair through either a top attachment or pincers, both of which are constructed of spongy material which soaks up the dye mixture from the mixing spiral. The invention also provides a latex tube which prophylactically isolates the dyed hair such that the dye does not spread in an undesired manner.

During the average person's life, his or her hair eventually loses pigment and grey hair appears. For those wishing to cover up the grey hair, the common method is to simply dye the entire head of hair. The dyeing process is an essentially basic practice of placing dye material on the hair, so that the hair takes on the covering color rather than the underlying grey.

Other people wish to streak or add highlights to their hair. This is a fairly expensive and time-consuming process, as each individual tuft of hair desired to be dyed must be physically separated from the rest of the hair, then have dye material placed on that tuft and, finally, have the dyed material isolated from the other parts of the person's hair.

No matter what the reason for wishing to color hair by a method other than dyeing the entire head of hair at once, there exists a problem relating to how to dye individual hairs or smaller or larger tufts of hair without smearing the dye on other hairs, and performing the dyeing operation in an efficient and cost-effective method. A brief review of the present methods will support the contention that current methods do not provide a satisfactory way in which individuals and hair care professionals can dye individual hair or tufts of hairs.

One present method requires a person to don a rubber cap with multiple small openings. A steel hook is then used to pull hair tufts out through the openings in the rubber cap, which are then dyed. To dye the hair, a paintbrush or small spade is used to take dye and apply it to the tuft by sliding the brush or spade along the tuft. After all the tufts of hair pulled through the rubber cap are dyed, another rubber cap is slipped over the first rubber cap to prevent the tufts from drying as the dye deposits the dye color on the hair tufts (it is important to the dyeing process that the hair does not dry out too quickly, which can happen if the hair tuft is exposed to air immediately after being dyed).

The other commonly used method is to have the hair care professional manually separate and isolate the tuft desired to be dyed, stretch it and keep it suspended in the air, separated from the rest of the hair, or to lay it on a long, narrow strip of aluminium foil. Dye is then applied to the hair tuft, after which the tuft is wrapped in aluminium foil that protects the dyeing tuft of hair from prematurely drying out and keeps it from dripping dye on the other portions of the hair.

The first method can be painful, while the other one requires skill, experience, and a lengthy amount of time. Both methods have an inherent risk that either the dye can fall on the remaining hair or that the dye leaks through the aluminium foil. Both methods also require a hair care professional, as it is extremely difficult if not impossible to dye one's own hair using these methods.

Thus, there exists a need for a device which can be used by either a hair care professional or an individual to dye hair, by which dye, comprising either a single dye/developer mixture or a partitioned amount of dye material and developer which can be mixed in an enclosed container by either manual mixing or shaking, can be applied to a desired portion of hair, whether that is an individual hair or a tuft of hair of varying size.

An additional problem with the current methods is that once the dye material is mixed with developer and is exposed to air, it begins an irreversible drying process such that any unused part of the mixture must be thrown away. This waste results in a number of undesirable effects, including higher cost due to the need to use a larger quantity of materials, shortened working time as once the mixture is exposed to air, the hair care professional has a certain amount of time to perform the work before the mixture becomes unworkable, and the environmental damage that results from throwing away the toxic chemicals. Thus, it is desirable to have a device which can be used to dye hair but does not expose all of the dye material/developer mixture to air such that it begins to cure, but rather only uses the amount necessary to perform the desired colouring without wasting the entire mixture.

The current invention meets these needs with a single invention which address all of the above concerns, namely, a roughly cylindrical body which forms a dye cavity in which one or more dye partitions can be filled, where dye materials are pressed out through screw drive or compression means, and where the dye materials are protected from air until extruded, such that unused portions can be stored rather than thrown away. There are numerous iterations of this invention, designed to meet the varying needs of people desiring to color their hair ranging from individuals who would like to dye their hair every couple of months to hair care professionals who, with this invention, can perform many hair colourings each day. The invention teaches devices which hold in an airtight compartment both pre-mixed dye mixtures and bodies which hold separate compartments or partitions for dye material and developer. In this preferred embodiment the dye partitions have piston heads which are forced by pressure into the dye partitions such that both dye material and developer are forced into a mixing spiral which mixes them together. The mixture of dye material and developer is then applied to a person's hair through either a top attachment, which can come in a variety of shapes and sizes ranging from narrow brushes to broad spades, or pincers which can open and grasp individual hairs or hair tufts, where both the top attachments and pincers are constructed of spongy material which soaks up the dye mixture from the mixing spiral. The invention also provides a latex tube which prophylactically isolates the dyed hair such that the dye does not spread in an undesired manner.

SUMMARY OF THE INVENTION

It is a principal object of the invention to provide a device enable persons having only a limited number of grey hairs to dye only the individual grey hairs, without depositing or spilling dye chemicals on other hair that has retained its natural color.

It is another principal object of the invention that a user of the invention be able to put streaks in their hair through the use of the invention with one or more different colors or accents.

It is another object of the invention that tufts of hair of varying sizes can be colored.

It is an additional object of the invention that individual hairs can be colored.

It is a further object of the invention that a user of the invention can quickly and easily change the color of the dye to be applied to the hair.

It is another object of the invention to enable the dyeing of the hair tufts by depositing the dye by a simple dragging-through of pincers with a sponge rubber soaked with dye, by which the desired tuft is embraced.

It is an additional object of the invention to provide an extension element that enables a person to dye the hair or hair tuft all the way to the hair root.

It is a further object of the invention to increase the potential working speed of an individual or hair care professional when dyeing hair tufts.

It is also an object of this invention that by increasing the potential working speed, the cost of having one's hair dyed are reduced over current commercial rates.

It is another object of the invention that the simple function of the invention allows individuals to dye their own hair at home or in another location of their choosing.

It is also an object of this invention that the method of hair dyeing made possible by this invention is simple enough such that non-hair care professionals without any formal or informal education in hair care can dye their own hair by themselves at their home.

It is another object of the invention that the invention have at least two components which are mixed together only when a tuft or individual hair is ready for dyeing, such that the unused components remain "inactive" and can be used later.

A further object of the invention is to promote low cost hair dyeing through the mixing of only as much of the inactive ingredients as is necessary for use at that time.

It is also an object of the invention to promote ecology and environmental protection through decreasing the amount of toxic chemicals that are dumped down the drain after a batch of active hair dye was mixed and not completely used.

Further objects of the invention include the ability of the device to rotate such that the ejector openings seal shut, thereby preventing both the exposure of the dye mixture to air and the accidental leakage or expulsion of dye mixture from the openings.

An additional object of the invention allows a user to dye only that part of the hair that has grown after the last dyeing, as well as dyeing the part of tufts of hair or individual hairs closest to the skin.

Another object of the invention is that a user without any significant specialisation, training, or skill can perform hair dyeing in a manner superior to past methods previously obtainable only by hiring hair care professionals, with less preparation time than was previously required even by hair care professionals.

A further object of the invention is to provide that the various dye partitions enables the filling of various volumes and various mixing ratios of the dyeing ingredients, which, in combination with various piston areas and openings through which the liquid is being pressed out from the container enables a precise dosing and mixing of dyeing components in the desired ratio.

Additional objects of the invention include the teaching of an elastic protective ring device with the latex or aluminium protection hose which can be applied during dyeing the hair tufts, for protecting the hair that is not intended to be dyed from the contact with the dyed hair, as well protecting the dye on the dyed tuft from an undesirable quick drying that would interrupt the dyeing process.

It is an additional object of the invention to avoid manual mixing of ingredients, as is the norm in the hair care industry, as the invention provides for the packing of the inactive ingredients in separate containers which are mixed inside of the invention when ready to use, thereby not only saving time but also decreasing the health risks for those who are currently mixing the toxic chemicals by hand.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

BRIEF DESCRIPTION OF THE FIGURES

The drawings of the invention present the variety of iterations of the invention and explain the interrelationships and functions of the particular invention parts.

DETAILED DESCRIPTION OF THE FIGURES

Figure 1:
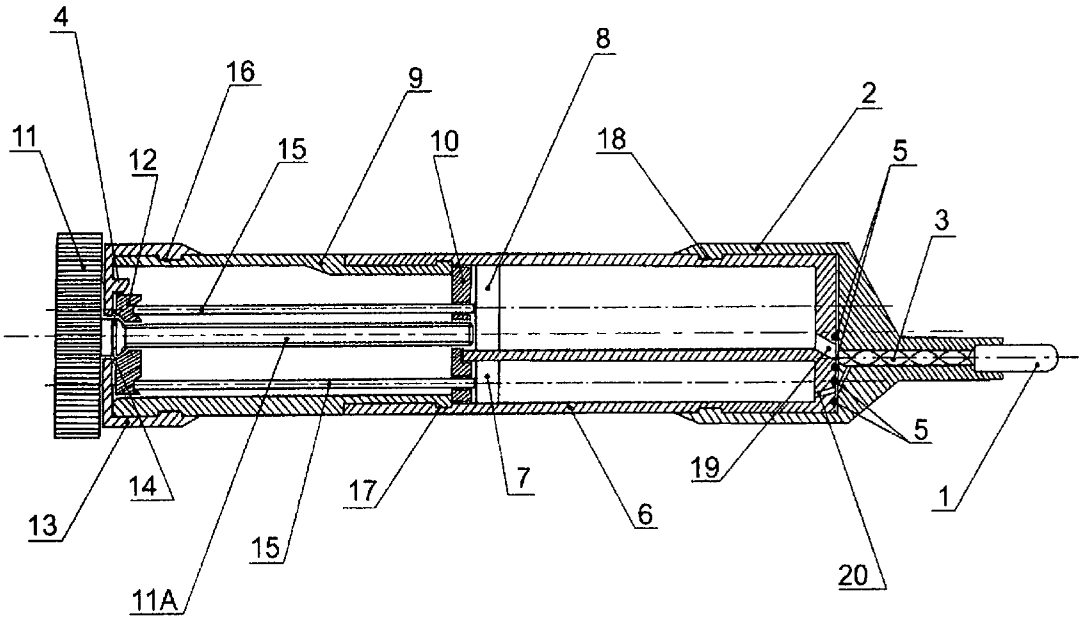
FIG. 1 is a side, cross-sectional view of the assembled invention in its iteration with two-component dye device for precise dyeing where the ingredients are mixed and then pressed out by the turning of the adjustable wheel through a mixing spiral and then applied to individual hairs or tufts of hair through a top attachment.

The device for the precise dyeing of individual hairs and for hair tufts has an outer body, comprised of two mated halves, or manufactured as a single cylinder. The device also has an interior cavity, in which there is a dye container with one or more dye partitions. The contents of the dye partition(s) is extruded through an extrusion end of the device by pressure put upon the contents by a piston head attached to a piston axel which fits through the rear portion of the dye container. Applying pressure to the piston axel can be accomplished through thumb pressure, the turning of an adjustment wheel that causes a variety of screw drive mechanisms to force the piston axel forward, or compression/injection mechanisms. On the front of many iterations is a top carrier, which houses, optionally, a mixing channel in which lays a mixing spiral, means for attachment of pincers to clasp individual hair or hairs, and a location for a top attachment. The top carrier is attached to the body by means of an annular bulge and a groove.

For the iteration of the invention where the dye material and developer are mixed during application, inside of the body are one or more containers for the dye components which have front end openings for extruding the dye. The openings are decentred from the body axis in such a way that by turning the top carrier for about 45 degrees the openings open or close as desired. As pressure is applied to the rear portion of the dye partitions, the dye material and developer are forced into a mixing channel, in which a mixing spiral sits. The mixing spiral is a carefully engineered mixing device with a variety of counter opposed spiral segments with holes such that by the time the dye material and developer reach the end of the mixing channel, they are completely mixed. At the point of extrusion, there can be placed either pincers or a top attachment, both of which are constructed of spongy material that is easy to clean and soaks up the dye material/developer mixture for application to hair. Once the dye material/developer mixture is exposed to the air, it becomes activated and begins its curing and drying process.

For the iteration of the invention where the dye material and developer are not mixed inside of the body, there are two basic approaches. First, in a single-use application, the device is sold with a pre-mixed mixture of dye material/developer inside of the body, filling up a single dye partition, such that a user merely needs to put pressure on the partition, through thumb, compression/injection, or an adjustable wheel, such that the mixture is extruded onto the pincers or top attachment, whereupon it is applied to the hair and begins to cure and dry upon exposure to the air. Second, in multiple-use applications, the dye partition can be refilled, while the actual process of extruding the dye is that same as with the single-use application. As with the version in which the dye material and developer are mixed within the body, the pre-mixed versions also can have an opening that is decentred from the body axis in such a way that by turning the top carrier for about 45 degrees the opening opens or closes as desired. At the point of extrusion, there can be placed either pincers or a top attachment, both of which are constructed of spongy material that is easy to clean and soaks up the dye material/developer mixture for application to hair. Once the dye material/developer mixture is exposed to the air, it becomes activated and begins its curing and drying process.

All iterations of the invention offer a number of optional components, including an airtight, protective cover which can protect the pincers and/or top attachments from drying out or being damaged should a user of the invention drop it. There is also an optional elastic protecting ring device by which individual hairs or hair tufts can be isolated from the rest of the hair and grasped, then dyed from the root up, with a latex hose being rolled out around the dyed hair or hair tuft as the dye is applied, such that a user of the invention does not need to worry about accidentally dyeing other portions of the customer's head.

FIG. 1 is a side, cross-sectional view of the assembled invention in its iteration with a two-component dye device for precise dyeing where the ingredients are mixed and then pressed out by the turning of the adjustable wheel through a mixing spiral and then applied to individual hairs or tufts of hair through a top attachment. The device has a rear part (9) and an injector body (6) which has dye containers, into which the different dye ingredients—namely the dye material and the developer—are stored. Inside of each dye container is a piston head (7 and 8), attached to piston axels (15), which push the contents of each dye container into a mixing channel, in which a mixing spiral (3), discussed and described in more detail in FIG. 3, mixes the two ingredients before they are extruded through the end of the device. The container volumes can be different depending on the desired ingredient-mixing ratio. The usual preparations are mixed in ratios ranging from 1:3 to 1:1. The exact ratio of the ingredients is regulated by the size of the opening section through which the ingredients are pressed out of the container and by the area of pistons (7) and (8).

On the rear part of the invention there is an adjustable wheel (11) with a screw drive (11A). By turning the wheel (11), the screw drive (11A) also turns, which, in turn, moves a nut (12) wound on the screw (11A) linearly. The nuts (12) press down on the piston axels (15) which press the piston heads (7 and 8) against the dye ingredients, pushing the dye ingredients into the mixing spiral (3). The pistons uniformly press out the ingredients from the containers and the ratio is determined by the diameter of openings (19) and (20) through which they are pressed out and by the diameter of the container, and by the diameters of the pistons. It is contemplated that a version with adjustable openings is possible, such that the exact ratio between dye material and developer can be adjusted as desired.

After the particular ingredients are pressed out of the partitions, they enter into the mixing spiral (3) that is located in a top carrier (2). By passing through the mixing spiral (3), the ingredients are mixed together and upon exit from the mixing spiral (3) through the two annular seals (5), the mixture is extruded to a top (1) made of spongy material. The top (1) soaks up the mixture, thereby readying it for application to hair.

The top carrier (2) is attached to the body (6) with a groove (18) on the body and with the annular bulges on the inner side of the top carrier (2) into which the groove fits. This allows the top carrier (2) to be turned about its axis without increasing the distance between the two parts, and also enables an impermeable closing of the openings (19 and 20) so that the openings can be shut off or opened as desired by the user.

The openings (19) and (20) on the body (6) are placed off-center of the body (6) such that the turning of top carrier (2) about its axis enables the pressing-out of the contents from the container in one position, while by turning top carrier (2) for about 45 degrees causes the openings (19) and (20) to become completely closed. In such a way the leaking of the ingredients and its mixing is prevented.

The top carrier (2) is made in such a way that in its opening at the extrusion point of the mixing channel a chosen top attachment for dyeing can be inserted, or the pincers for tuft dyeing can be placed. In such a way the dosage of the necessary amount of ingredients and the preserving of the container contents is enabled.

At the rear end of the injector body (6) the rear part of the body (9) is attached by means of groove (17) on the inner side of body (6) which corresponds to an annular bulge on the rear part of body (9) into which the groove (17) fits. The rear part of the body (9) serves to connect the body (6) with the assembly for pushing the pistons.

The inner wall of body rear part (9) is not entirely round but has a flat section or nut holder (4) against which the flat portion of the nut (12) rests, preventing the turning of nut (12) and securing in such a way its linear motion. The rear part of the body (9) abuts an alignment plate (10) that serves for supporting the piston axels (15) and keeping the screw in the axial position. There are holes in the alignment plate just large enough to allow the piston axels (15) to pass through, thereby allowing the piston axels to apply pressure to the piston heads (7 and 8) without allowing any of the contents of either partition to backflow into the rear part of the device. The piston heads (7 and 8) are also manufactured with precision such that none of the contents of the dye partitions backflows behind them either, which enhances the efficiency of the device.

The rear part cover (13) serves to connect the adjustable wheel (11) with the screw drive (11A) and the pistons, making assembling the invention simple and thus economical. The rear part cover (13) is connected with the body rear part (9) by means of the annular bulge and groove (16) on body rear part (9). The adjustable wheel (11) with the screw drive (11A) is connected with body rear part cover (13) by a securing device (14). For the precise dyeing of individual hairs, it is necessary to insert one of the top attachments or pincers as illustrated in other illustrations into the opening of the extrusion end of the mixing spiral (3).

Figure 2:
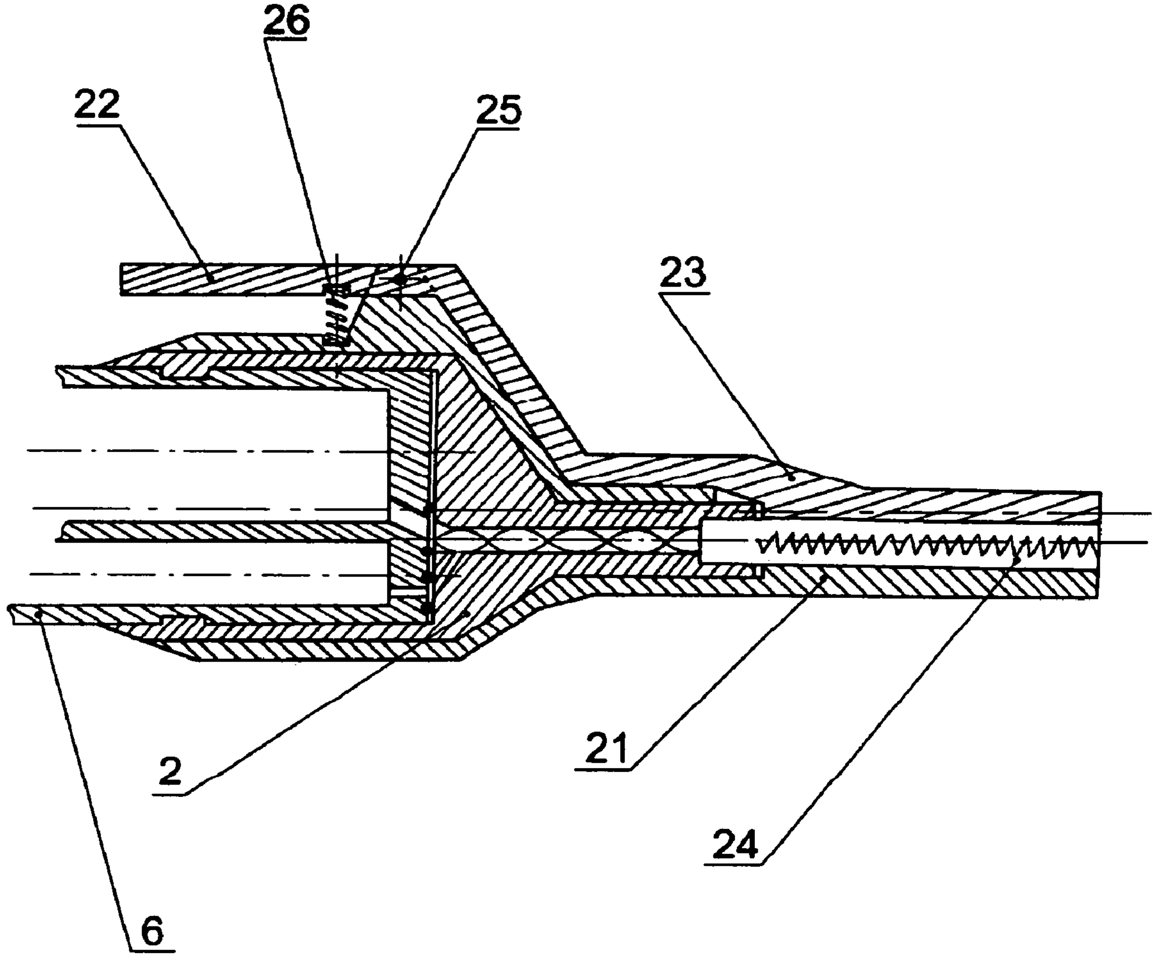
FIG. 2 is a side, cross-sectional view of the invention with a set of pincers attached to the top carrier for dyeing hair tufts using the two-component dyeing system where the mixed dye material is pressed out by turning the adjustable wheel.

FIG. 2 is a side, cross-sectional view of the invention with a set of pincers attached to the top carrier for dyeing hair tufts using the two-component dyeing system where the mixed dye material is pressed out by turning the adjustable wheel. If the user of the invention wishes to dye hair tufts, then the top for precise dyeing (1 from FIG. 1) can be taken out and replaced with a pincer device, which attaches to the top carrier (2). The pincers device for dyeing hair tufts are placed on the invention which consist of a pincers body (21) with lower pincers arm, a pincers upper part (23) with an opening lever (22), an axle (25) that connects the pincers upper part (23) with the opening lever (22) and enables the opening of the pincers, spiral spring (26) that closes the pincers after being compressed during the opening of the pincers and secures the pressure of the spongy rubber jaws (24) on the tuft.

When a user places the pincers body (21) onto the carrier (2), the spongy rubber jaws (24) has a round shape in its rear part that enters into the opening of top carrier (2) and comes into contact with the pressed dye which flows onto it and soaks it. Basically, the end of the spongy rubber with a flat cross section replaces the top attachment from FIG. 1, and serves the same function of soaking up the extruded dye material/developer mixture. The front part of spongy rubber jaws (24) is cut through into two pieces and the upper part is attached to the pincers upper part (23), while its lower part is attached to the lower arm that is a part of pincers body (21). When the dye is pressed out of the container into body (6), it comes in contact with the spongy rubber jaws (24) and soaks into it.

By pressing on the opening lever (22) of the pincers upper part (23), the pincers upper part (23) rotates about axle (25) and the spongy rubber jaws (24) open. After the hair tuft that is selected to be dyed is put in the spongy rubber jaws (24), the lever (22) of pincers upper part (23) is released, whereupon a spiral spring (26) presses the pincers upper part (23) and they close the spongy rubber jaws (24). Then, the spongy rubber jaws (24) that have been soaked with dye presses onto the hair tuft. By dragging the spongy rubber jaws (24) over the tuft, the dye from spongy rubber jaws (24) remains on the tuft and dyes it.

Figure 3:
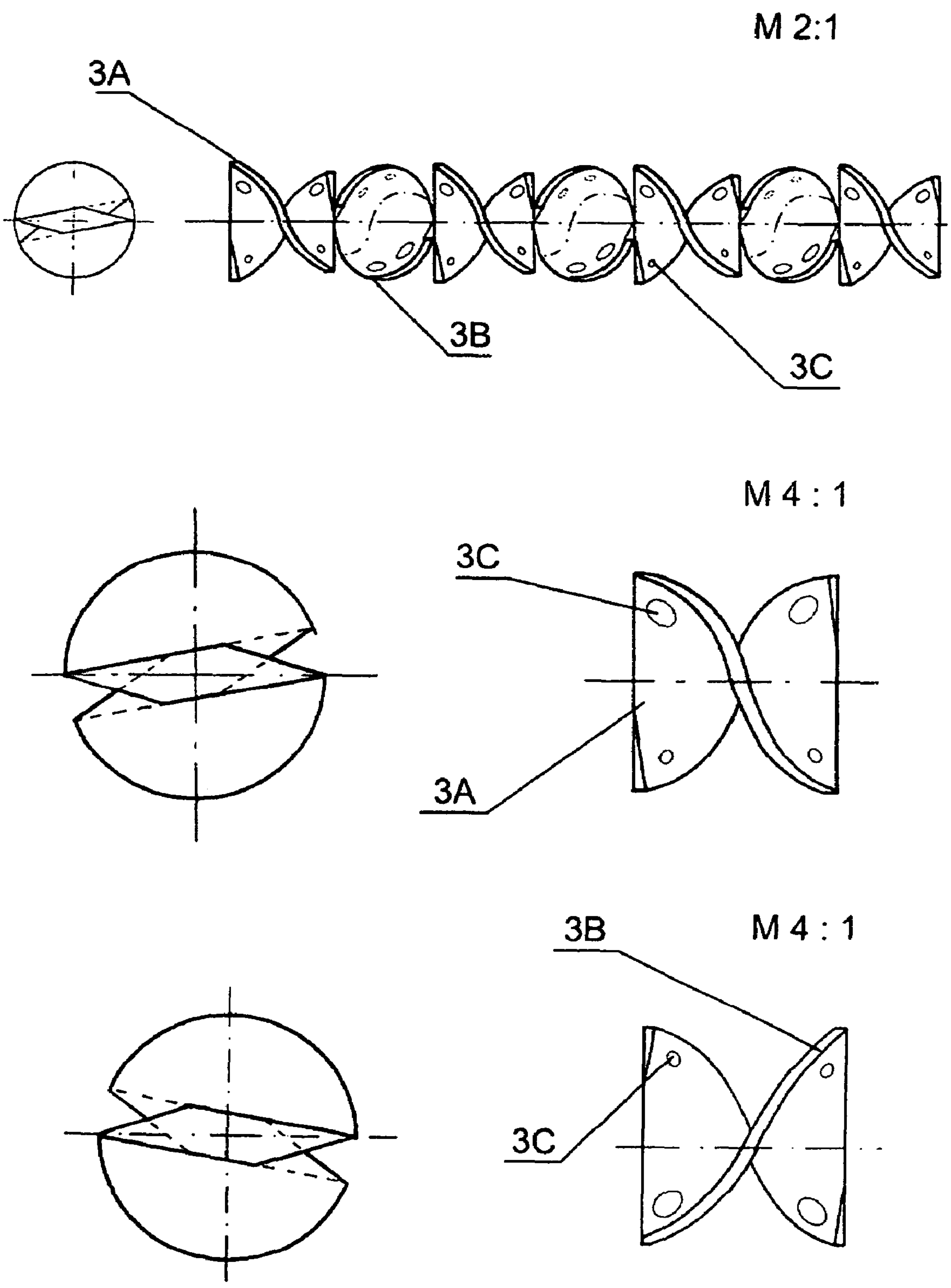
FIG. 3 contains top and side views of the mixing spiral for mixing the ingredients, and the top and side views of the mixing spiral segment with a left hand view of the spiral winding, and of the spiral segment with a right hand view of the spiral winding. It is apparent from this figure how the two parts of a dye mix are mixed through being pushed through the spiral.

FIG. 3 contains top and side views of the mixing spiral for mixing the ingredients, and the top and side views of the mixing spiral segment with a left hand view of the spiral winding, and of the spiral segment with a right hand view of the spiral winding. It is apparent from this figure how the two parts of a dye mix are mixed through being pushed through the spiral. After the particular ingredients are pressed out of the dye partitions, they enter into mixing spiral (3 in FIG. 1). The mixing spiral (3 in FIG. 1) is placed in top carrier (2 in FIG. 1). The mixing spiral consists of interconnected segments made in spiral form, where each next segment has a counter-winding spiral as compared with the spiral segment in front of, a behind, it. Therefore, if the first segment spiral (3A) winds from the left to the right, the next segment (3B) is connected at 90 degrees and winds from the right to the left, and the third segment has again a spiral winding from the left to the right and is made with a shift of 90 degrees to the preceding one, the second spiral segment (3B). To mix the ingredients, each of the ingredients is pressed out into one half of the spiral until it is full, such that one ingredient fills the left channel of the spiral and the other ingredient fills the right channel of the spiral, and following its shape both ingredients arrive to the end of the first segment and meet the second segment that is placed in a way that the section axis intersects at 90 degrees the section axis of the first segment and divides the left and right channel in two halves. Therefore, the half amount of the ingredient from the left channel and the half amount of the ingredient from the right channel enter and fill up the same upper channel of the second segment, and the half amount of the ingredient from the right channel enter into the second lower channel of the second segment. When they are pressed through several segments, the ingredients are completely intermixed.

On the spiral periphery there are spiral periphery openings (3C) which are designed and manufactured in a way that during the pressing-through period through the spiral segments the ingredients pass from one channel into another and additionally intermix. While the pressure is equal on the ingredients that fill up the left and right channel, the openings in the walls of spiral (3C) are made in a way that, watching from the direction where the ingredients arrive into the spiral, the openings (3C) have a greater diameter than the openings on the opposite side of the wall. In other words, the cross-section of the openings has the shape of the truncated cone. As the pressure per unit area is equal, the greater area of the opening at one side gives a greater pressure per unit area. Therefore, the pressure at the side with the greater opening diameter overcomes the pressure on the opposite side, thereby enabling the ingredients to further mix when passing through the spiral periphery openings (3C).

The spiral of each segment turns for 150 degrees, thereby providing a sufficient length for mixing the components through the spirals and spiral periphery openings (3C). The mixing channel is also of sufficient length to enable the mixing of the components during their passage through it.

Figure 4:
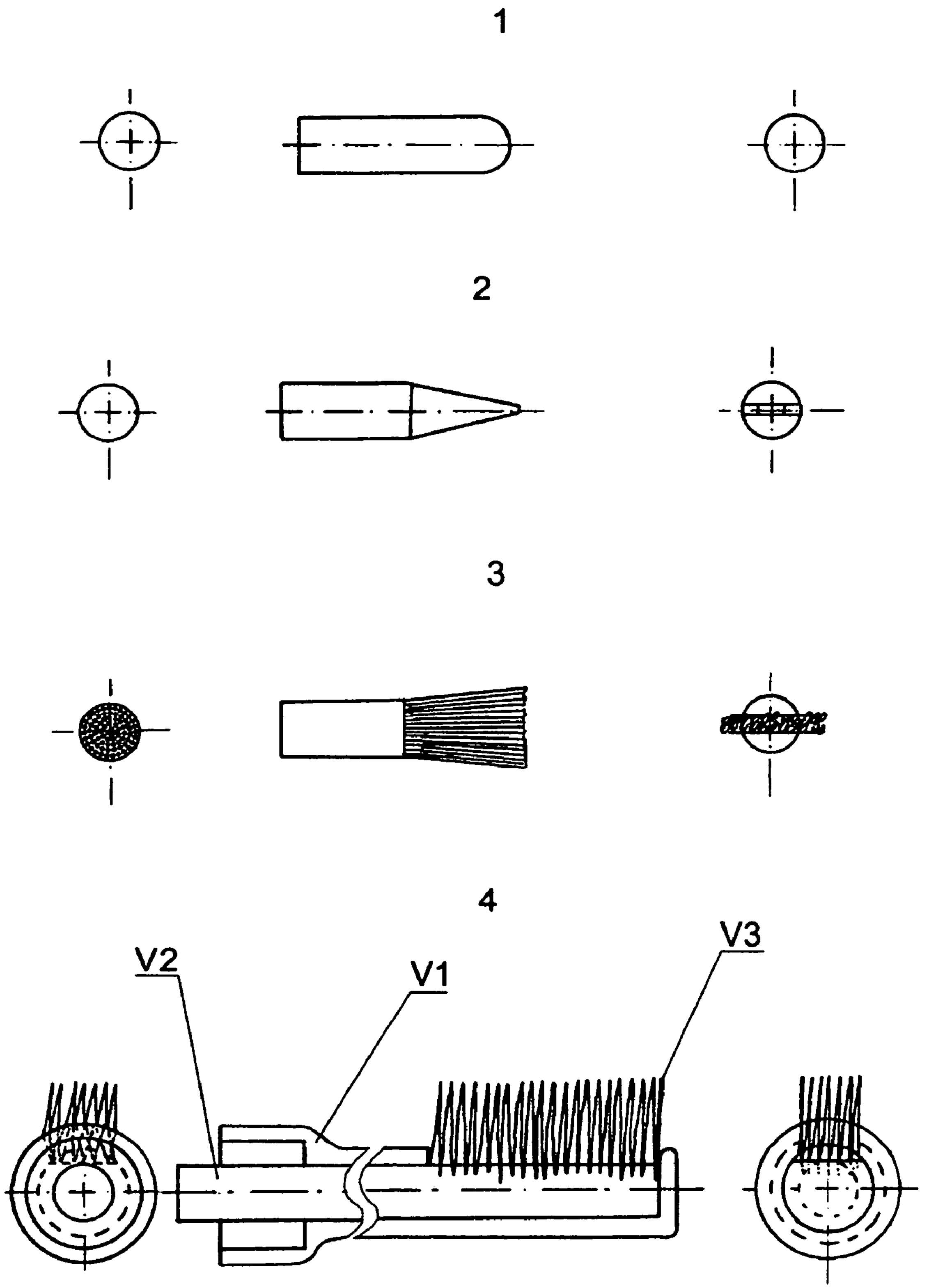
FIG. 4 contains drawings (side, top and front view) of various extensions or top attachments for the precise dyeing of individual hairs and smaller hair tufts, showing the wide variety of top attachments envisioned, ranging from thin brushes to large spades.

FIG. 4 contains drawings (side, top and front view) of various extensions or top attachments for the precise dyeing of individual hairs and smaller hair tufts, showing the wide variety of top attachments envisioned, ranging from thin brushes to large spades.

Top 1 is a round shape with a semi-spherical ending, and it serves for a richer depositing of the dye. It is inserted into the top carrier (2 in FIG. 1 and other Figures). Top 2 is a round shape with the flat ending, and it serves for the precise depositing of the dye onto hair. Top 3 has a rear part that enters into the opening of carrier of round shape, while its ending is flat. It consists of a set of thin threads and serves for a somewhat richer depositing of the dye. It is inserted into top carrier. Top 4 placed on top carrier with its front side protruding. It has body (V1) of round shape and in it spongy rubber (V2) is placed that is soaked with the dye from the container. The body (V1) is partly open at the upper front side, and on this place a thin brush (V3) is pressed into a segment of spongy rubber (V2). Top 4 serves for dyeing smaller hair tufts.

Figure 5:
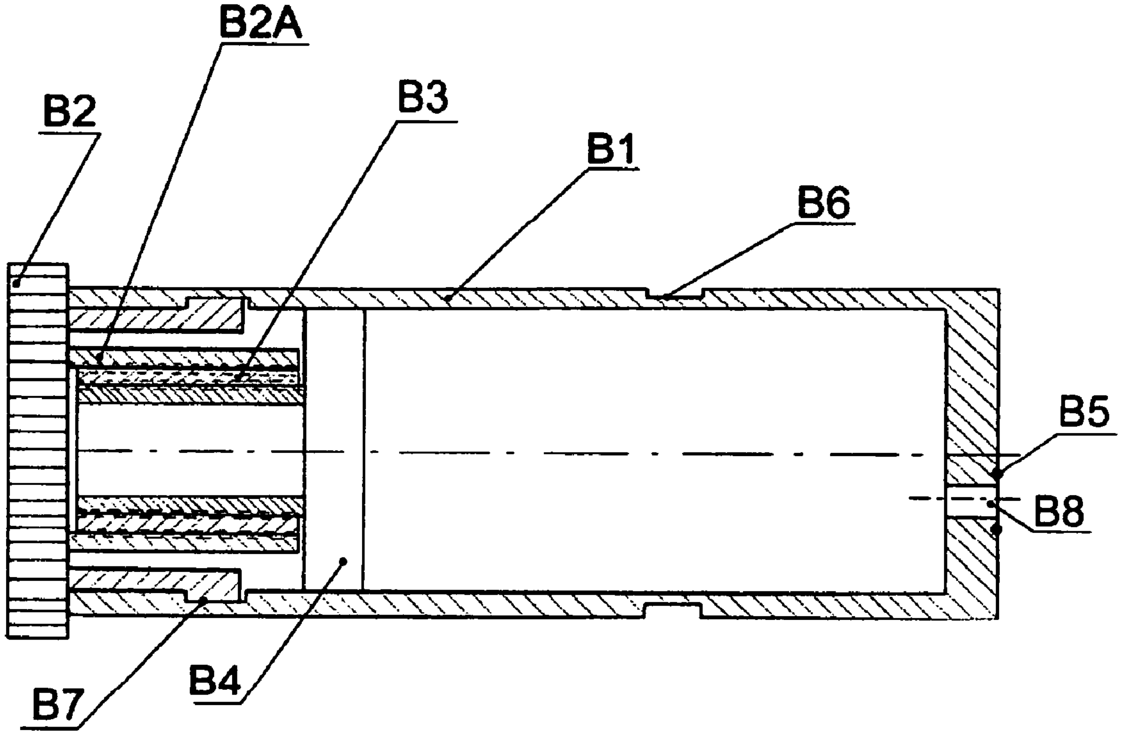
FIG. 5 is a side, cross-sectional view of an iteration of the invention for the application of the one-component dye where the dye is pressed out by turning the adjustable wheel, which then telescopically expands and causes a piston to force the pre-mixed dye material/developer mixture out of an opening.

FIG. 5 is a side, cross-sectional view of an iteration of the invention for the application of the one-component dye material/developer mixture where the mixture is pressed out by turning the adjustable wheel, which then telescopically expands and causes a piston to force the pre-mixed dye material/developer mixture out of an opening. In this iteration, there is only one major body part, called here the injector body (B1), which houses both the dye container and the means by which the pressure is applied to the mixture in the dye container. In the injector body (B1) there is a dye container for the mixture of dye material and developer, a piston (B4), which, in this figure, is an oval piston, for pressing out the dye mixture, and a screw system for pressing the piston. It is envisioned that this iteration can be sold as either a one-use product where the user buys the pre-mixed dye material/developer with a certain color of dye material, then uses it and disposes of the injector body once it is empty, or as a multiple-use version where the user can refill the dye container with his or her own mixtures, then clean and reuse the injector body after each use. An adjustable wheel (B2) turns an inner threaded tube (B2A) which turns tube with inner and outer threads (B3), which engages threads in the axel of the piston (B4), and thereby pushes the piston (B4) against the contents of the dye container. In this figure, the piston (B4) has an oval shape, and the injector body (B1) is also oval in shape. This prevents the piston (B4) from rotating as the tube with inner and outer threads engages and turns threads on the axel of the piston (B4). An alternative means of ensuring that the piston did not rotate would be to have a ridge along the injector body which fit into a corresponding cavity in the piston head, such that the piston could only run longitudinally when pressurized, rather than dissipating the force by spinning around on its axis.

A major advantage of this iteration of the invention is that it is relatively short compared with other iterations, which is important for the aesthetic appearance and simple handling of the invention.

An opening (B8) on the injector body (B1) is placed off-center with respect to the axis of the injector body (B1) in a way that the turning of top carrier (2 in FIG. 1 and other Figures) enables the extrusion of the dye material/developer mixture from the container in one position, while by turning the carrier (2) for approximately 45 degrees the opening is completely closed. In such a way the leaking of dye is prevented and air is excluded from the dye container, thereby preventing the curing and drying of the dye material in the dye container. Around the opening (B8) a groove is an annular seal (B5) that ensures the impermeability of the opening to air. The injector body (B1) is connected by means of a groove (B6) to the top carrier (2 in FIG. 1 and other Figures) in such a way that in the opening of the top carrier for insertion of a top attachment or pincers is aligned with the opening (B8).

Figure 6:
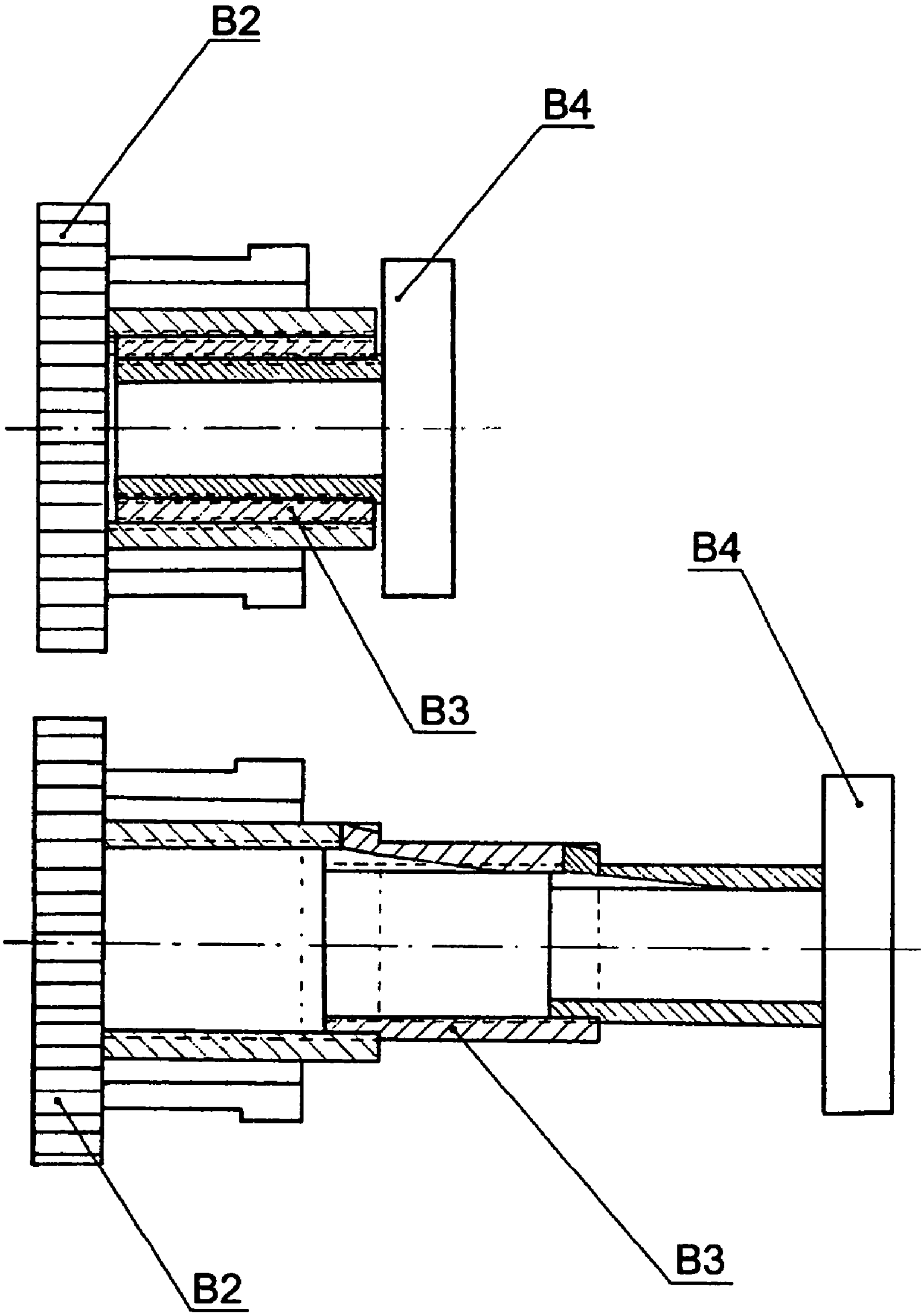
FIG. 6 is a side, cross-sectional view of the invention shown in FIG. 5 where the threaded tubes have expanded to their full capacities.

FIG. 6 is a side, cross-sectional view of the invention shown in FIG. 5 where the threaded tubes have expanded to their full capacities. Here, the piston head (B4) has been fully extended by the turning of the adjustable wheel (B2), which has rotated the inner threaded tube (B2A) which turned the tube with inner and outer threads (B3), which engaged the threads in the axel of the piston (B4), and thereby pushed the piston (B4) against the contents of the dye container as the unit expanded in a telescoping fashion.

Figure 7:
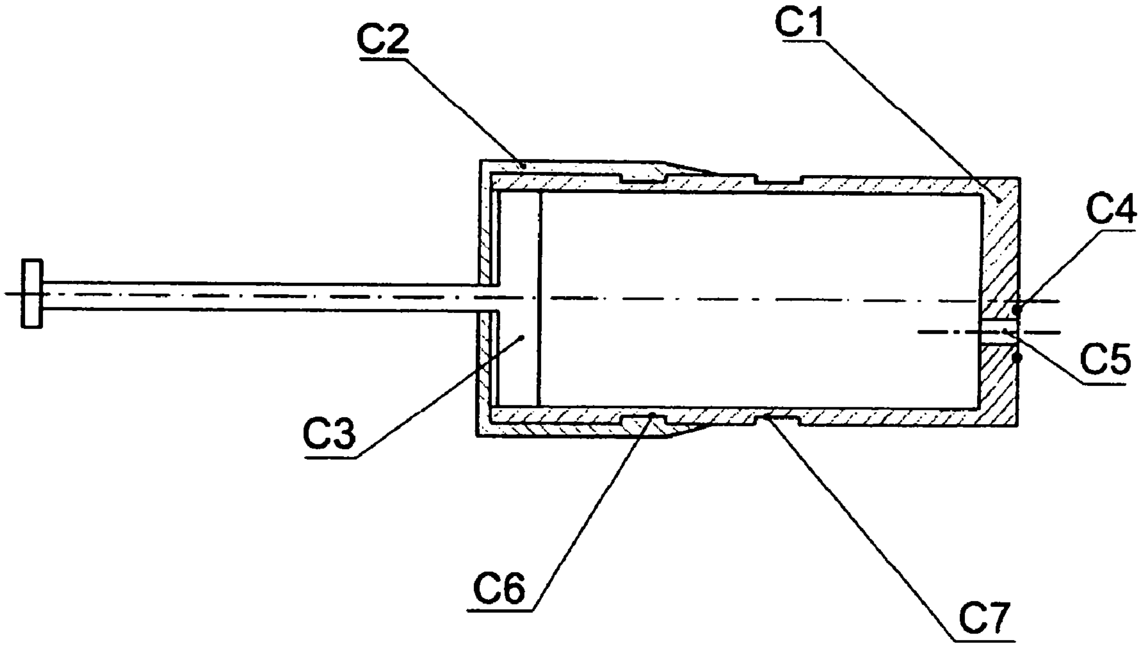
FIG. 7 is a side, cross-sectional view of an iteration of the invention for the application of a dye material/developer mixture where the mixture is pressed out by an injection method.

FIG. 7 is a side, cross-sectional view of an iteration of the invention for the application of a dye material/developer mixture where the mixture is pressed out by an injection method. This iteration can be sold "as is" or can be inserted into a body (not shown in this iteration) which can have alternative means to apply pressure to the piston, and which can accommodate a top carrier. The injector body (C1) is of a cylindrical shape and open at its rear end. In the injector body there is a container with a pre-mixed dye material/developer mixture, and a piston (C3) for pressing out the dye mixture. When the piston (C3) is pressed, it presses out the dye from the dye container through an opening (C5) with an annular seal (C4). At the rear portion of the injector body there is groove (C6) by which the injector body (C1) is connected with a rear part (C2) that serves as the cover for the injector body (C1). On the front part of the injector body (C1), the opening (C5) is set off-center with respect to the axis of injector body (C1) in a way that by turning the top carrier (2 in other Figures but not shown here) the dye mixture can be pressed out through the opening (C5) from one position, while by turning the top carrier for about 45 degrees the opening (C5) is completely closed, thereby preventing the leaking of dye. The top carrier is optionally attached to the injector body by a groove (C7) on the middle of the injector body (C1), such that a top carrier can be attached to the injector body to allow the use of top attachments and pincers for more precise dyeing of hair.

Figure 8:
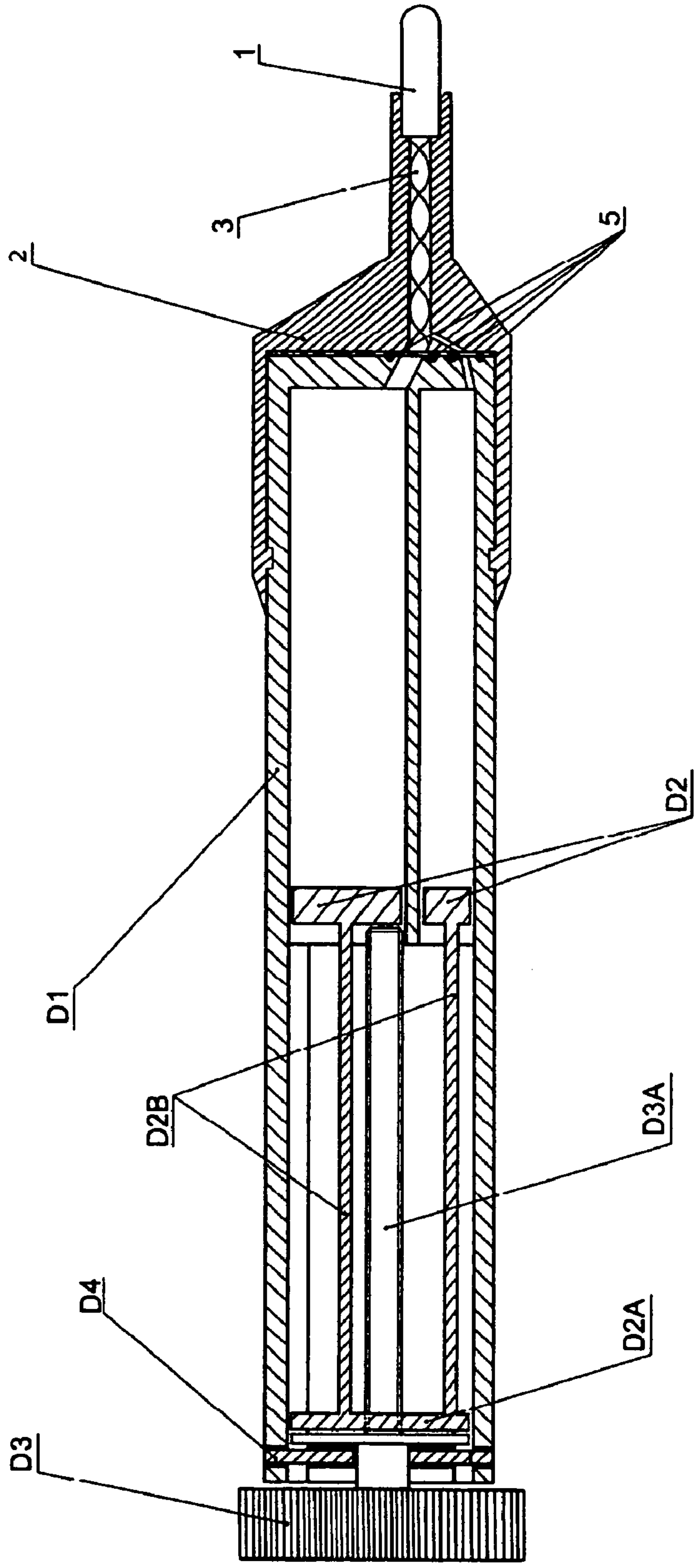
FIG. 8 is a side, cross-sectional view of the assembled invention for the use of the two-component dye device where the dye is pressed out by turning the adjustable wheel which rotates a threaded screw drive, which then forces two piston axels against two piston heads, which then drive dye material and developer from their partitions through a mixing spiral and out into the spongy material of a top attachment.

FIG. 8 is a side, cross-sectional view of the assembled invention for the use of the two-component dye device where the dye is pressed out by turning the adjustable wheel which rotates a threaded screw drive, which then forces two piston axels against two piston heads, which then drive dye material and developer from their partitions through a mixing spiral and out into the spongy material of a top attachment. A major difference between the invention as illustrated by this figure and that in FIG. 1 is that the iteration in FIG. 1 has a body consisting of two main parts while the iteration of FIG. 8 has a one-part body. In the injector body (D1) there are dye partitions with ingredients for the hair dyeing—namely the dye material and developer, where the containers can be made in a variety of sizes and with different capacities depending on the dye material/developer ratio desired.

On the rear part of the injector body (D1) there is a adjustable wheel (D3), a little plate (D4) which secures the adjustable wheel (D3) to the inner workings of the injector body (D1), and a threaded little plate (D2A), which moves linearly up and down a threaded screw drive (D3A). By turning the adjustable wheel (D3), the threaded screw drive (D3A) is turned, which moves the threaded little plate (D2A) linearly, forcing piston axels (D2B) linearly and thereby putting pressure on piston heads (D2). The threaded little plate (D2A) is made in a circular shape with two symmetrical indentations. The inner wall of the body (D1) has two projections which mate with the indentations on the threaded little plate, such that a twisting of the piston axle (D2B) is prevented, and ensure that movement of the adjustable wheel (D3) is translated into linear motion of the threaded little plate, piston axels, and piston heads.

After the individual ingredients are pressed out from the dye partitions, they enter into the mixing spiral (3) for mixing, where the spiral is located in the top carrier (2). By passing through the mixing spiral the ingredients are intermixed and on the exit from the mixing spiral (3) to the top attachment (1) which is made of spongy material. The extruded dye material/developer mixture is then soaked up by the top attachment (1), and the top attachment (1) is ready for hair dyeing. The top carrier (2) has an opening into which any one of the extensions for the precise dyeing (top attachments V1, V2, V3 or V4 from FIG. 4) can be placed, or for the tuft dyeing the attachment top for precise dyeing (1) is taken away and on the top carrier (2) the pincers for tuft dyeing are attached.

The injector body (D1) is connected to the top carrier (2) by a groove on the injector body and the annular bulges on the inner side of the top carrier (2), what enables the turning of top carrier (2) about the axis without increasing the distance between these two parts. This enables the impermeable closing of the opening for the pressing-out of the dyeing ingredients by means of annular seals (5). The openings on body (D1) are placed out-of-centre with respect to the body (D1) in a way that the turning of the top carrier (2) about its axis enables the pressing-out of the contents from the container in one position, while by turning the top carrier (2) for about 45 degrees causes the openings to be completely closed. In such a way the leaking of the ingredients and their mixing and exposure to air is prevented.

At the rear end of the injector body (D1), there is a little plate (D4). The little plate connects and aligns the adjustable wheel (D3) with the injector body and the threaded screw drive (3DA). The threaded screw drive serves as a support, and secures its position in the center. It is of rectangular shape with a slot having the width equal to the diameter of screw (D3A). The slot is made to the center of the little plate (D4), what enables the insertion of the little plate into the body (D1) after the pistons with axles and little plate (D2) are set and into which the adjustable wheel with the screw (D3) is wound. The little plate (D4) is inserted into the slots in the body (D1), which are cut into two inner walls of the body (D1), which are constructed as two parallel planes.

Figure 9:
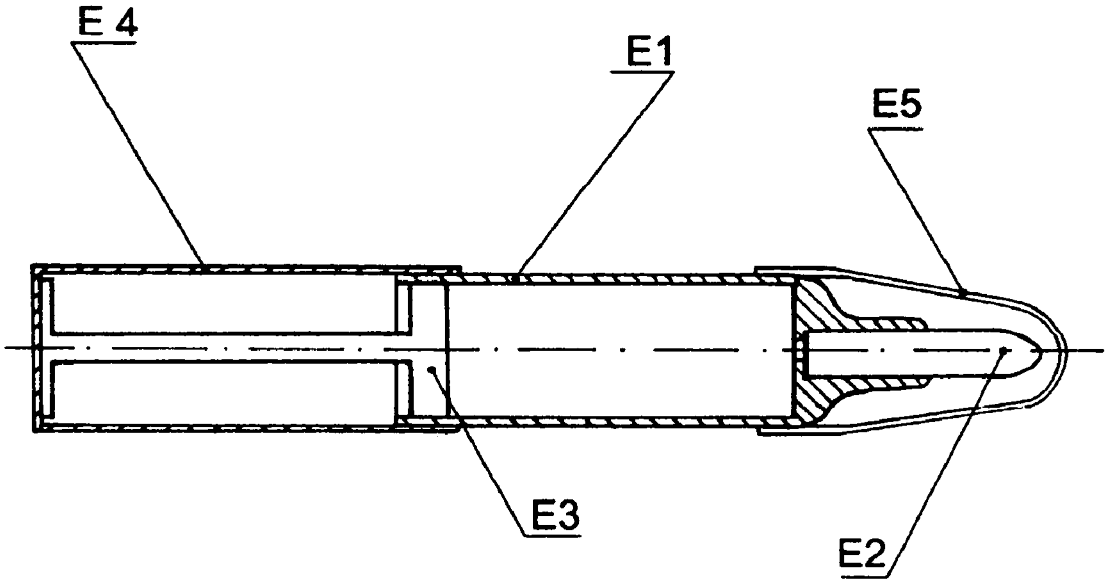
FIG. 9 is a side, cross-sectional view of the assembled invention for the application of a pre-mixed dye material/developer mixture, that is pressed out by an injection method utilizing a rear compression end over the thumb rest of FIG. 7, such that this iteration can be used either as a pre-mixed, single use applicator, or as a refillable, multiple use applicator.

FIG. 9 is a side, cross-sectional view of the assembled invention for the application of a pre-mixed dye material/developer mixture, that is pressed out by an injection method utilizing a rear compression end over the thumb rest of FIG. 7, such that this iteration can be used either as a pre-mixed, single use applicator, or as a refillable, multiple use applicator. The injector body (E1) is manufactured in a cylindrical shape, and serves as the container of pre-mixed dye material and developer. It is fully open at its rear end, and on the front end it has an opening through which the dye is pressed out of the container. Into this opening a top attachment (E2) made of spongy material is inserted, which is soaked with dye. In the injector body (E1) is a piston (E3) with an axle for applying pressure to the dye container. The axle is protected by and enclosed by a cylindrical shell or rear compression end (E4) that fixes the axle and gives a nicer aesthetic appearance along with a convenient flat end upon which a user can put pressure. The top attachment (E2) is made of spongy material and protected, optionally, by a cover (E5).

When the invention is to be used, the optional cover (E5) is taken off and the injector body (E1) is grasped between the thumb and the forefinger, and the rear compression end (E4) is put on the palm of the hand. The injector body (E1) is pressed by the fingers towards the palm, and the rear compression end (E4) presses on the axle of the piston (E3), so that the piston presses the dye out of the dye container onto the top attachment (or pincers as envisioned in another iteration). The pressed-out dye soaks the top attachment's spongy material and thereby prepares the top attachment to transfer dye onto the hair.

Figure 10:
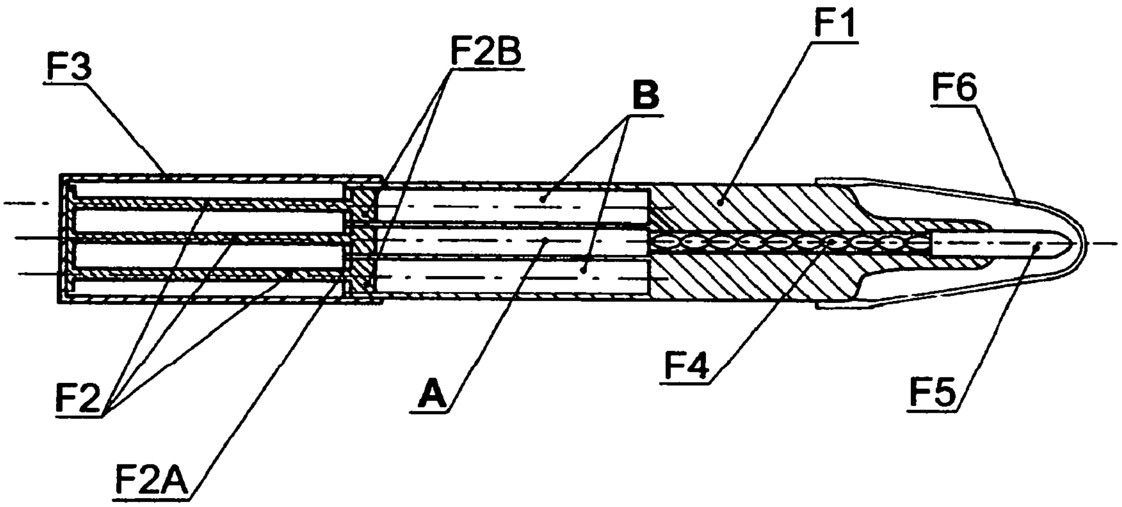
FIG. 10 is a side, cross-sectional view of the assembled invention for application of dye material and developer, both in separate partitions, where the contents of the two partitions are pressed out by an injection method, where the piston axels that push the piston heads against the dye material and developer are covered by a rear compression end, which, when pressurized by the user of the invention, causes the dye material and developer to flow through the mixing channel and mixing spiral, whereupon the mixture of dye material and developer is then extruded onto a top attachment made of spongy material, which is then used to transfer the dye material/developer mixture to the hair. This iteration utilizes a rear compression end such that this iteration can be used either as a pre-mixed, single use applicator, or as a refillable, multiple use applicator. This figure also shows the optional cover, which creates an airtight seal over the top attachment to retard the drying of the active mixture of dye material and developer that has been absorbed by the top attachment. Finally, this figure illustrates an iteration of the invention where the dye material partition occupies the entire outer portion of the body cavity and the developer partition occupies an inner partition completely enclosed within the outer, dye material partition.

FIG. 10 is a side, cross-sectional view of the assembled invention for application of dye material and developer, both in separate partitions, where the contents of the two partitions are pressed out by an injection method, where the piston axels that push the piston heads against the dye material and developer are covered by a rear compression end, which, when pressurized by the user of the invention, causes the dye material and developer to flow through the mixing channel and mixing spiral, whereupon the mixture of dye material and developer is then extruded onto a top attachment made of spongy material, which is then used to transfer the dye material/developer mixture to the hair. This iteration utilizes a rear compression end such that this iteration can be used either as a pre-mixed, single use applicator, or as a refillable, multiple use applicator. This figure also shows the optional cover, which creates an airtight seal over the top attachment to retard the drying of the active mixture of dye material and developer that has been absorbed by the top attachment. Finally, this figure illustrates an iteration of the invention where the dye material partition occupies the entire outer portion of the body cavity and the developer partition occupies an inner partition completely enclosed within the outer, dye material partition.

The injector body (F1) has, in this iteration, centrally placed dye partitions, and is manufactured in a cylindrical shape. It is fully opened at the rear end, and at the front end has openings through which the components are pressed out from their containers. The ratio of the components is determined by the diameter of the openings through which they are pressed out and by the area of pistons (F2A). The dye partitions are made in a way that the outer, cylindrical wall of body (F1) is also the outer wall of outer container (B), and is built to contain the dye material. At its axis an inner container (A) is built, which is also of cylindrical shape but of smaller diameter, assigned for the placement of the developer.

Concentric pistons with axles (F2) that press out the components are made in a way such that the smaller piston, which is inserted into inner container (A), is of a round shape and on its axis is set the axle by which it is pressed. The piston entering the outer container is also of round shape but in its center is an opening having the size of the outer wall of inner container (A)—basically a piston with a donut hole in the center. At the front side of the injector body (F1) there is the cylindrical bore inside of which is a mixing spiral (F4) which mixes the pressed-out components. At the extrusion point of the mixing spiral is a bore large enough to accommodate a top attachment (F5) made of spongy material, which soaks up the dye mixture extruded from the mixing spiral. In this Figure, the top attachment is covered by an optional protective cover (F6), which protects the top attachment from getting dirty or damaged should the invention be dropped, and forms an airtight seal around the top attachment thereby retarding the curing and drying process that begins to occur upon exposure of the dye material/developer mixture to air.

Figure 11:
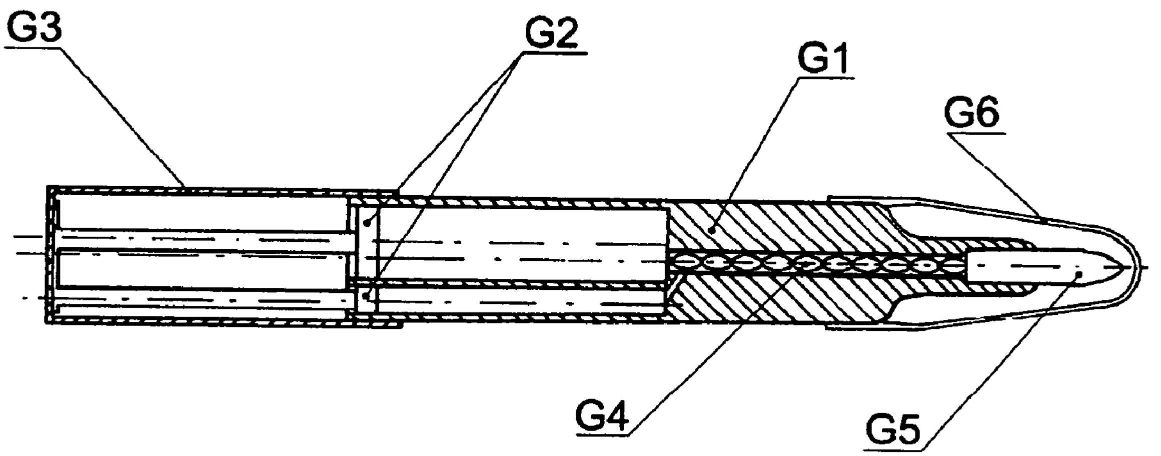
FIG. 11 is a side, cross-sectional view of the assembled invention for application of dye material and developer, both in separate partitions, where the contents of the two partitions are pressed out by an injection method, where the piston axels that push the piston heads against the dye material and developer are covered by a rear compression end, which, when pressurized by the user of the invention, causes the dye material and developer to flow through the mixing channel and mixing spiral, whereupon the mixture of dye material and developer is then extruded onto a top attachment made of spongy material, which is then used to transfer the dye material/developer mixture to the hair. This iteration utilizes a rear compression end such that this iteration can be used either as a pre-mixed, single use applicator, or as a refillable, multiple use applicator. This figure also shows the optional cover, which creates an airtight seal over the top attachment to retard the drying of the active mixture of dye material and developer that has been absorbed by the top attachment. Finally, this figure illustrates an iteration of the invention where the dye material partition occupies one part of the body cavity and the developer partition occupies an adjacent partition such that the developer partition is not completely enclosed within the outer partition of dye material.

FIG. 11 is a side, cross-sectional view of the assembled invention for application of dye material and developer, both in separate partitions, where the contents of the two partitions are pressed out by an injection method, where the piston axels that push the piston heads against the dye material and developer are covered by a rear compression end, which, when pressurized by the user of the invention, causes the dye material and developer to flow through the mixing channel and mixing spiral, whereupon the mixture of dye material and developer is then extruded onto a top attachment made of spongy material, which is then used to transfer the dye material/developer mixture to the hair. This iteration utilizes a rear compression end such that this iteration can be used either as a pre-mixed, single use applicator, or as a refillable, multiple use applicator. This figure also shows the optional cover, which creates an airtight seal over the top attachment to retard the drying of the active mixture of dye material and developer that has been absorbed by the top attachment. Finally, this figure illustrates an iteration of the invention where the dye material partition occupies one part of the body cavity and the developer partition occupies an adjacent partition such that the developer partition is not completely enclosed within the outer partition of dye material.

The injector body (G1) is very similar to the iteration described in FIG. 10, except the iteration illustrated by FIG. 11 has parallel dye partitions rather than having a partition for the developer enclosed in the partition for the dye material. At the front side of the injector body there is a mixing spiral (G4) for mixing, and a top attachment (G5) made of spongy material with, in this figure, an optional cover (G6). In the "single-use" iteration, the invention is sold with the top cover in place, such that there is no curing or drying of any dye material/developer mixture prior to the use of the invention. The rear end of the injector body (G1) is covered by a plate, through which there are openings for the heads of pistons (G2). The containers are placed in the symmetry axis one alongside the other, and in the containers are also pistons with axles (G2). The axles are built in the middle of pistons (G2) and connected with the pressing little plates on their end. It is also contemplated that this version of the invention could be sold as a multiple-use device, where the plate and rear compression end could be removed and the dye material and developer replenished.

To use this iteration of the invention, the cover (G6) is taken off, the injector body (G1) is grasped between the thumb and forefinger, and the rear, flat part of rear compression end (G3) is placed on the palm of the hand. The injector body (G1) is pressed by the fingers towards the palm, and rear compression end (G3) presses on the axles of pistons (G2), whereupon the pistons (G2) press the components out of the container into the mixing spiral (G4). After being mixed in the mixing spiral (G4), the dye material/developer mixture is extruded onto the top attachment (G5) (or pincers in an alternate iteration), where the dye mixture is soaked up by the top attachment and can be transferred onto the hair.

Figure 12:
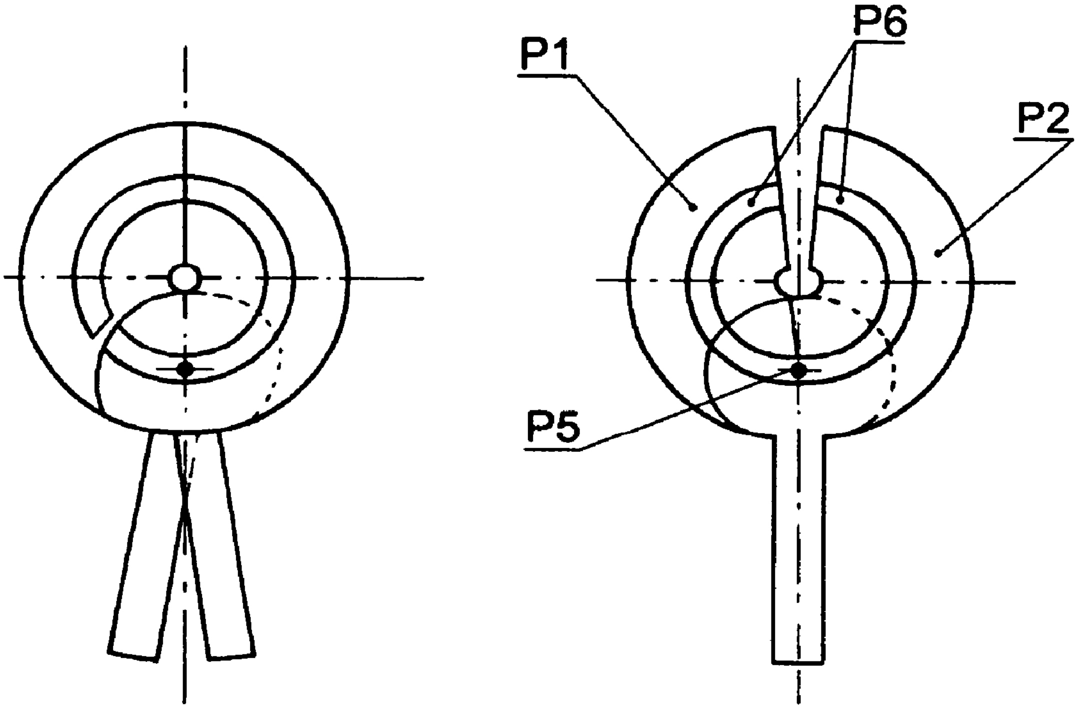
FIG. 12 is a top and side views of the elastic protecting ring device which protects the dyed tufts in both open and closed positions, showing how the elastic ring can be rotated to close off the openings, and how the half rings can be closed upon a hair or hair tuft to isolate it. By pressing the levers of half rings and the elastic ring, the hair tuft is separated from the remaining hair and pulled through the central opening, whereupon the device lowers down to the root, where the levers are released. A latex hose is pulled over the tuft and placed on an annular stand. After dyeing the hair or hair tuft, the latex hose is unrolled and spread over the tuft, thereby allowing a user of the invention to effectively and efficiently isolate the dyed hair and prevent it from leaking dye onto the rest of the hair.
Figure 12:
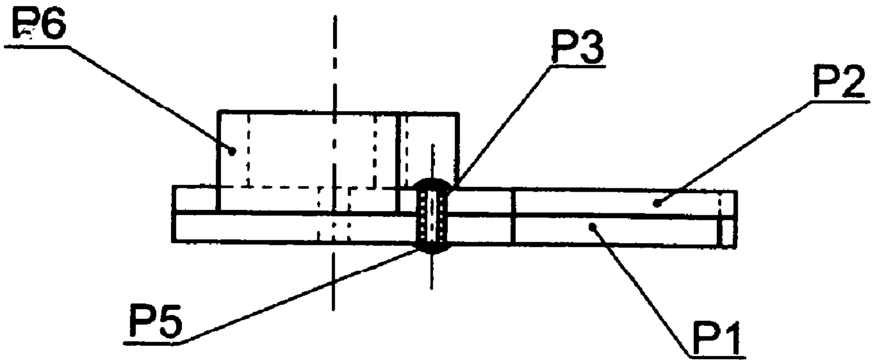

FIG. 12 is a top and side views of the elastic protecting ring device which protects the dyed tufts in both open and closed positions, showing how the elastic ring can be rotated to close off the openings, and how the half rings can be closed upon a hair or hair tuft to isolate it. By pressing the levers of half rings and the elastic ring, the hair tuft is separated from the remaining hair and pulled through the central opening, whereupon the device lowers down to the root, where the levers are released. A latex hose is pulled over the tuft and placed on an annular stand. After dyeing the hair or hair tuft, the latex hose is unrolled and spread over the tuft, thereby allowing a user of the invention to effectively and efficiently isolate the dyed hair and prevent it from leaking dye onto the rest of the hair.

The elastic protecting ring device consists of two half rings with arms, a left half ring (P1) and a right half ring (P2), a reverse spring (P3), a connecting axle (P5) and a latex hose (P4). In the released position, half rings (P1) and (P2) fit tightly in a way that they make a fully circle in the center of which there is an opening that holds tight the tuft to be dyed. When the lever of left half-ring (P1) and the lever of right half-ring (P2) are pressed by two fingers, the two half rings move away from each other and the center of the unit is opened up. The hair tuft to be dyed is then drawn through this passage up to the central opening and the elastic protecting ring is lowered to the root of the hair, after which the levers of half rings (P1) and (P2) are released. The reverse spring (P3) presses half rings (P1) and (P2), thereby closing the ring and squeezing the tuft at the root. The latex or aluminium hose (P4), folded into a ring is drawn over the tuft and uncoiled from its coiled location on the annular stand (P6) formed by connecting left half ring (P1) and right half ring (P2). After dyeing the tuft, latex or aluminium hose (P4) is spread the full length over the tuft, protecting the dye from undesirable fast drying and protecting the rest of the hair from undesired dyeing.

Figure 13:
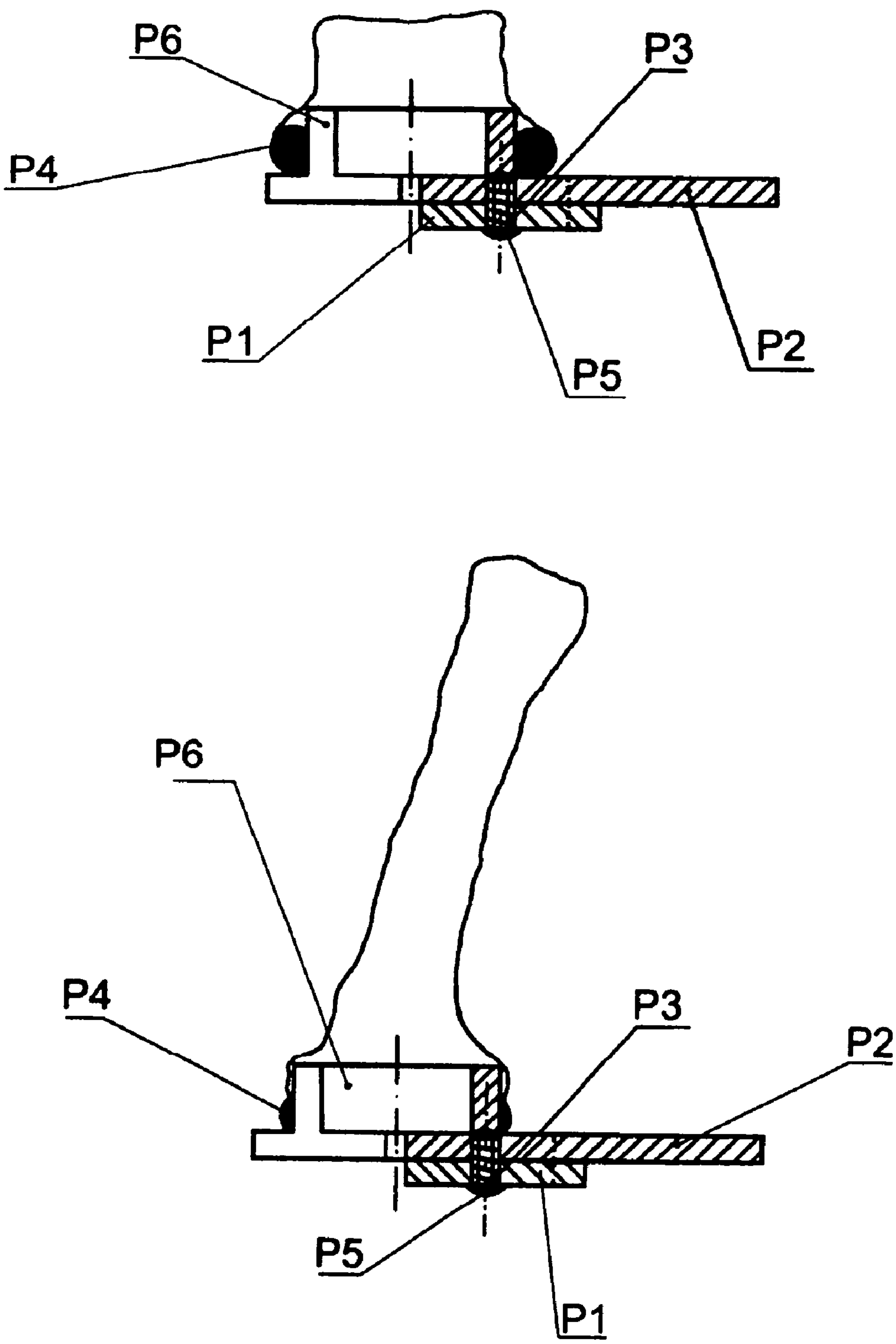
FIG. 13 is a side, cross-sectional view of the elastic protecting ring device with specific attention paid to the method of protecting the dyed tufts with the latex hose and how the latex hose unrolls to accomplish this protection.

FIG. 13 is a side, cross-sectional view of the elastic protecting ring device with specific attention paid to the method of protecting the dyed tufts with the latex hose how the latex hose unrolls to accomplish this protection.

Figure 14:
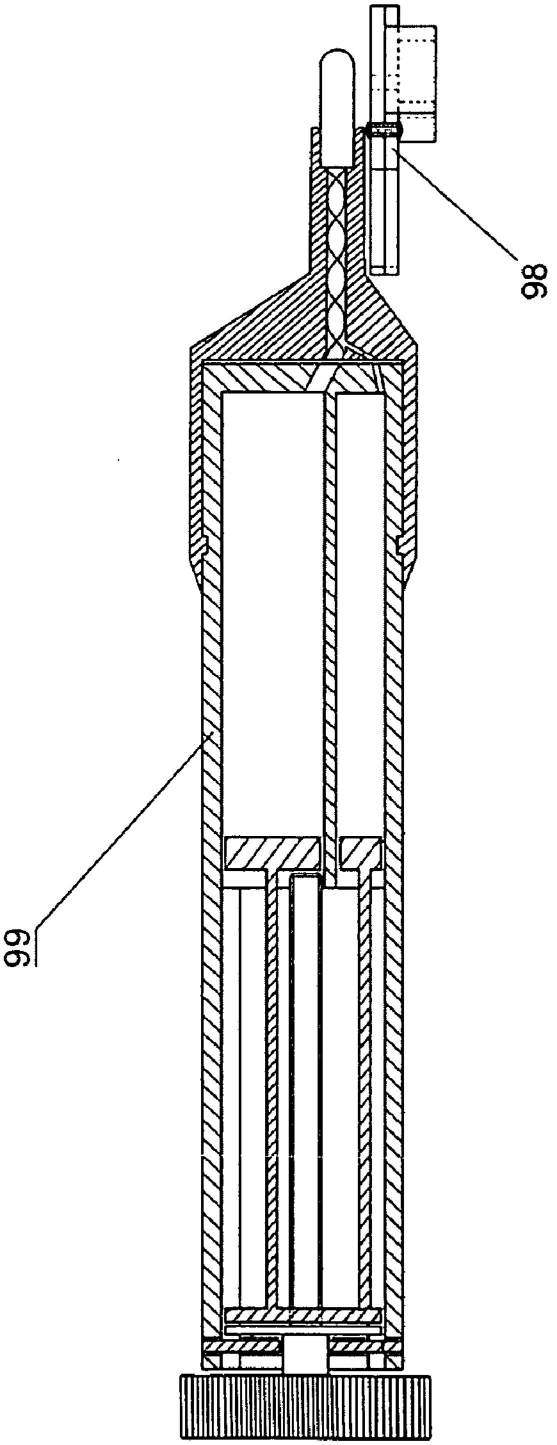
FIG. 14 is a side view of the elastic protecting ring device and the dye device.

FIG. 14 is a side view of the elastic protecting ring device and the dye device. The elastic protecting ring (98) can be utilized next to the tip of the dye device (99) whereby the tuft of hair can be isolated and dyed to the root. While the elastic protecting ring (98) is utilized next to the tip of the dye device (99) in this figure, other configurations are possible without departing from the scope of the claimed invention.

In order to clarify the terminology used in the claims, the substance used to color hair is referred to as "dye". The "dye" is comprised of "dye material", which is the colored dye before it is mixed with a developer, and a "developer", which, when mixed with the "dye material", activates the "dye material" for coloring hair. Some iterations of the invention have two dye components—one for dye material and the other for developer—such that when the two components are mixed, the developer activates the dye material and a dye is extruded and ready for dyeing the hair. Other iterations have pre-mixed combinations of dye material and developer, where the mixture remains inactive until extruded from the body of the invention and exposed to air. Thus, the term "dye components" can refer to either two partitions, with one for dye material and the other for developer, or to one partition which is, or can be, filled with a mixture of dye material and developer. In either case, the dye components, whether dye material and developer that are mixed in the invention or a pre-mixed combination of dye material and developer, does not become activated until exposed to air. When a mixture of dye material and developer is exposed to air, it begins to "cure", that is, perform its coloring action and at the same time begin to dry out, such that it has a limited lifetime within which it can effectively dye hair. As such, one of the invention's main creative advances is in preventing the unwanted, expensive, and environmentally destructive activation of a larger quantity of dye material/developer mixture than is immediately necessary to perform the hair coloring as desired at any certain time.

I claim:

1. A device for precise dyeing of individual hairs and for dyeing selected tufts, comprising:

a body, where, the body is roughly cylindrical in shape and defines a cavity, in which there exists a dye container, and where the body comprises a rear body end with means of applying pressure to the dye container inside of the body and an extruding end, where, the extruding end is comprised of a flat, circular plate with one or more openings and one or more annular seals surrounding the one or more openings, one or more partitions for dye components, located inside the dye container, where, the dye partitions have an end portion such that the unused dye components in the dye container are retained in the dye container in unused form and are not exposed to air prior to their extrusion, a cylindrical body which defines a cavity into which dye can be loaded, and an open top, where the dye components are comprised of substances that are not activated until they come into contact with air, a means for extruding a quantity of dye, where, the dye is passed onto the hair and, where the dye is a combination of dye material and developer, a means for applying the dye onto the hair where the means to apply the dye to hair is precise enough to allow the selective dyeing of individual hairs or tufts of hair, and an elastic protecting ring device, which is comprised of an annular stand which sits rotably above a right half ring and a left half ring, where the annular stand and the right half ring and the left half ring are rotably attached to one another by a connecting axel and a reverse spring which allows the left half ring and the right half ring to rotate under the annular stand such that a tuft of hair can be selected and partitioned off from the remaining hair, and a latex hose which is attached to the annular stand by means of an elastic band, and where, as the tuft of hair is passed through the elastic protecting ring device, the latex hose can be uncoiled such that the tuft of hair is prophylactically isolated from other hair such that any dye on the tuft of hair will not spill or seep onto other hair.

2. The device of claim 1, where the body is comprised of two parts, an injector body and a rear part, where the injector body has a groove circumscribing its inner circumference, and the rear part has an annular bulge located such that it removably attaches the two parts together.

3. The device of claim 1, where the body is comprised of three parts, an injector body, a rear part, and a rear part cover, where the injector body has a groove circumscribing its inner circumference, and the rear part has an annular bulge located such that they removably attach the two parts together, and the rear part also has a groove circumscribing its inner circumference, and the rear part cover has an annular bulge located such that they removably attach the two parts together.

4. The device of claim 1, additionally comprising a top carrier, located on the extruding end of the device, where the top carrier comprises an attachment end by which the top carrier is attached to the device, a bulge on its attachment end which fits into a corresponding groove on the extruding end of the device, a cavity for a mixing spiral, and an attachment cavity into which can be inserted a top or other means of applying the dye to hair.

5. The device of claim 4, where, the means for applying dye to hair is a set of pincers which can be removably attached to the top carrier, which comprise a pincers body with lower pincers arm, a pincers upper part, an opening lever, a spiral spring, an axel, and a spongy rubber jaws, where, the pincers body with lower pincers arm and the pincers upper part are removably attached to the top carrier, and the opening lever is compressably retained in a "closed" position by the spiral spring and held in position by the axel, such that when a user presses the opening lever with his or her thumb or other digit, the spongy rubber jaws open, which allows a user to place in the spongy rubber jaws a tuft of hair for dyeing, where the dye material is soaked up by the spongy rubber jaws after having been extruded from the extruding end of the device.

6. The device of claim 4, where, the top carrier can be rotated at least 45 degrees on its axis along its point of attachment with the injector body, and, where, by rotating the top carrier the openings become no longer aligned with the annual seals, such that the contents of the dye partition(s) can no longer be extruded from the device.

7. The device of claim 1, where, the means for applying the dye to hair is a top attachment, where, the top attachment consists of a round section of spongy material which can be removably attached to the extruding end of the device, where, the round sections can be made in a variety of shapes and are easily interchangeable, and readily soak up the dye material on the top, which allows the dyeing of tufts of hairs.

8. The device of claim 1, where, the extruding end of the device has a cover which is removably attached to the extruding end by means of a snap and groove, such that the cover can be removed easily, and, where, the cover forms an airtight seal over the extruding end such that drying out of the dye material is minimized.

9. The device of claim 1, where, the means for extruding the dye comprises a screw drive mechanism, which comprises an adjustable wheel which can be rotated by a user's thumb or fingers, and which, when rotated, turns a threaded screw drive, which, in turn, moves two threaded nuts along the screw drive, where, each nut has a flat section with threads which mate with the threaded section of the screw drive, where, each nut is retained in its track against the screw drive by, additionally, a nut holder, and, where the screw drive, in turn, drives two piston axels against two pistons, which are kept in alignment by securing devices at the end of the screw drive closest to the adjustable wheel and by plates at the end of the screw drive closest to the piston head, which put pressure on the two partitions, thereby extruding both dye material and developer through two openings and two annular seals into a mixing channel in which is located a mixing spiral which mixes the dye material and the developer, a top carrier which removably fits over the end of the body furthest away from the adjustable wheel and can serve as the location for attachment to a set of pincers and a top which collects the mixture of dye material and developer and can be used to apply the mixture to hair.

10. The device of claim 1, where, the means for extruding the dye comprises a screw drive mechanism, which comprises an adjustable wheel which can be rotated by a user's thumb or fingers, and which, when rotated, turns one or more inner threaded tubes, which, in turn, moves one or more tube with outer threads, which, in turn, drives one or more pistons which put pressure on one or more partitions, thereby extruding the contents of the one or more partitions through one or more openings and one or more annular seals.

11. The device of claim 1, where, the means for extruding the dye comprises a compression/injection device which comprises a rear compression end and an injector body, where the rear compression end consists of a cylindrical member with one closed end and one open end, where, by pushing down on the rear compression end, a user applies pressure to one or more piston axels, which drive one or more piston heads, which put pressure on one or more partitions, thereby extruding the contents of the one or more partitions through one or more openings and one or more annular seals, a top which collects the dye and can be used to apply the dye to hair.

12. The device of claim 1, where, the means for extruding the dye comprises a compression/injection device which comprises a compression piston mechanism, where the compression piston mechanism comprises a piston member which comprises a thumb rest, a piston axel, and a piston head, a compression cylinder which consists of a rear part removably attached by means of groove and annular bulge to an injector body, where the rear part has an opening large enough to accommodate the piston axel, such that when a user pushes down on the thumb rest, the resulting force on the piston head forces the dye through an opening in the injector body, and there is no spillage of the dye through the opening in the rear part, and, where, the opening on the injector body can accommodate a means of applying the dye material to hair.

13. The device of claim 1, where, the dye container has two partitions, where, one partition is filled with an amount of dye material and the other partition is filled with an amount of developer, where, the dye material does not become activated until mixed with developer and exposed to air.

14. The device of claim 13, where, the one or more pistons are two oval pistons with a threaded hole in the center of each oval piston, and the means for extruding a quantity of dye is an adjustable wheel attached to a screw drive with gears, where the screw drive with gears is adjacent to two piston screw drives, where the piston screw drives have gears which mate with the gears on the screw drive with gears, and threads, and the partitions are manufactured with oval shapes which mate with the oval shape of the oval pistons, such that the oval pistons can be forced down into the dye by the rotation of the piston screw drives and the screw drive threads which mate with threads on the hole in the oval piston.

15. The device of claim 13, where, the partitions are located with one partition adjacent and abutting the other partition, where the partitions are not located with one partition inside another partition.

16. The device of claim 1, where, the container has one partition into which dye material can be stored, where, the partition is filled with a mixture of dye material and developer.

17. The device of claim 16, where, the means for extruding the dye comprises a compression/injection device which comprises a rear compression end and an injector body, where the rear compression end consists of a cylindrical member with one closed end and one open end, where, by pushing down on the rear compression end, a user applies pressure to a piston axel, which drives a piston head, which puts pressure on a dye partition, where the partition is filled with a mixture of dye material and developer, thereby extruding the dye through an opening and an annular seal into a top which collects the dye and can be used to apply the dye to hair.

18. A device for precise dyeing of individual hairs and for dyeing selected tufts, comprising:

- a body, where the body is roughly cylindrical in shape and defines a cavity, in which there exists a dye container, and where the body comprises a rear body end with means of applying pressure to the dye container inside of the body and an extruding end, where the extruding end is comprised of a flat, circular plate with one or more openings and one or more annular seals surrounding the one or more openings,
- one or more partitions for dye components, located inside the dye container, where the dye partitions have an end portion such that the unused dye components in the dye container are retained in the dye container in unused form and are not exposed to air prior to their extrusion, a cylindrical body which defines a cavity into which dye can be loaded, and an open top, where the dye components are comprised of substances that are not activated until they come into contact with air, a means for extruding a quantity of dye, where the dye is passed onto the hair and, where the dye is a combination of dye material and developer, a means for applying the dye onto the hair where the means to apply the dye to hair is precise enough to allow the selective dyeing of individual hairs or tufts of hair, and a top carrier, located on the extruding end of the device, where the top carrier comprises an attachment end by which the top carrier is attached to the device, a bulge on its attachment end which fits into a corresponding groove on the extruding end of the device, a cavity for a mixing spiral, and an attachment cavity into which can be inserted a top or other means of applying the dye to hair, where the means for applying dye to hair is a set of pincers which can be removably attached to the top carrier, which comprise a pincers body with lower pincers arm, a pincers upper part, and opening lever, a spiral spring, an axel, and a spongy rubber jaws, where, the pincers body with lower pincers arm and the pincers upper part are removably attached to the top carrier, and the opening lever is compressably retained in a "closed" position by the spiral spring and held in position by the axel, such that when a user presses the opening lever with his or her thumb or other digit, the spongy rubber jaws open, which allows a user to place in the spongy rubber jaws a tuft of hair for dyeing, where the dye material is soaked up by the spongy rubber jaws after having been extruded from the extruding end of the invention.

19. The device of claim 18, where the body is comprised of two parts, an injector body and a rear part, where the injector body has a groove circumscribing its inner circumference, and the rear part has an annular bulge located such that it removably attaches the two parts together.

20. The device of claim 18, where the body is comprised of three parts, an injector body, a rear part, and a rear part cover, where the injector body has a groove circumscribing its inner circumference, and the rear part has an annular bulge located such that they removably attach the two parts together, and the rear part also has a groove circumscribing its inner circumference, and the rear part cover has an annular bulge located such that they removably attach the two parts together.

21. The device of claim 18, where the top carrier can be rotated at least 45 degrees on its axis along its point of attachment with the injector body, and, where, by rotating the top carrier the openings become no longer aligned with the annual seals, such that the contents of the dye partition(s) can no longer be extruded from the device.

22. The device of claim 18, where the extruding end of the device has a cover which is removably attached to the extruding end by means of a snap and groove, such that the cover can be removed easily, and where the cover forms an airtight seal over the extruding end such that drying out of the dye material is minimized.

23. The device of claim 18, where, the means for extruding the dye comprises a screw drive mechanism, which comprises an adjustable wheel which can be rotated by a user's thumb or fingers, and which, when rotated, turns a threaded screw drive, which, in turn, moves two threaded nuts along the screw drive, where, each nut has a flat a section with threads which mate with the threaded section of the screw drive, where, each nut is retained in its track against the screw drive by, additionally, a nut holder, and, where the screw drive, in turn, drives two piston axels against two pistons, which are kept in alignment by securing devices at the end of the screw drive closest to the adjustable wheel and by plates at the end of the screw drive closest to the piston head, which put pressure on the two partitions, thereby extruding both dye material and developer through two openings and two annular seals into a mixing channel in which is located a mixing spiral which mixes the dye material and the developer, a top carrier which removably fits over the end of the body furthest away from the adjustable wheel and can serve as the location for attachment to a set of pincers and a top which collects the mixture of dye material and developer and can be used to apply the mixture to hair.

24. The device of claim 18, where, the means for extruding the dye comprises a screw drive mechanism, which comprises an adjustable wheel which can be rotated by a user's thumb or fingers, and which, when rotated, turns one or more inner threaded tubes, which, in turn, moves one or more tube with outer threads, which, in turn, drives one or more pistons which put pressure on one or more partitions, thereby extruding the contents of the one or more partitions through one or more openings and one or more annular seals.

25. The device of claim 24, where the inner threaded tubes and the tubes with outer threads are nestled within the next larger size such that when the adjustable wheel is turned the inner threaded tubes and the tubes with outer threads expand in a telescoping fashion to put pressure on the one or more pistons.

26. The device of claim 24, where, the one or more pistons are two oval pistons with a threaded hole in the center of each oval piston, and the means for extruding a quantity of dye is an adjustable wheel attached to a screw drive with gears, where the screw drive with gears is adjacent to two piston screw drives, where the piston screw drives have gears which mate with the gears on the screw drive with gears, and threads, and the partitions are manufactured with oval shapes which mate with the oval shape of the oval pistons, such that the oval pistons can be forced down into the dye by the rotation of the piston screw drives and the screw drive threads which mate with threads on the hole in the oval piston.

27. The device of claim 18, where, the means for extruding the dye comprises a compression/injection device which comprises a rear compression end and an injector body, where the rear compression end consists of a cylindrical member with one closed end and one open end, where, by pushing down on the rear compression end, a user applies pressure to one or more piston axels, which drive one or more piston heads, which put pressure on one or more partitions, thereby extruding the contents of the one or more partitions through one or more openings and one or more annular seals, a top which collects the dye and can be used to apply the dye to hair.

28. The device of claim 18, where, the means for extruding the dye comprises a compression/injection device which comprises a compression piston mechanism, where the compression piston mechanism comprises a piston member which comprises a thumb rest, a piston axel, and a piston head, a compression cylinder which consists of a rear part removably attached by means of groove and annular bulge to an injector body, where the rear part has an opening large enough to accommodate the piston axel, such that when a user pushes down on the thumb rest, the resulting force on the piston head forces the dye through an opening in the injector body, and there is no spillage of the dye through the opening in the rear part, and, where, the opening on the injector body can accommodate a means of applying the dye material to hair.

29. The device of claim 18, where, the dye container has two partitions, where, one partition is filled with an amount of dye material and the other partition is filled with an amount of developer, where, the dye material does not become activated until mixed with developer and exposed to air.

30. The device of claim 18, additionally comprising a mixing channel and a mixing spiral, where the mixing channel is of sufficient length to mix the arriving dye material and developer, where the mixing spiral comprises a series of segments, where, each segment consists of a spiral part radiating out from a central axis in a twisting manner, where, each segment has one or more spiral periphery openings, where the spiral periphery openings have larger openings on one side of the segment than the other, where, the design of the spiral periphery openings encourage the mixing of the dye material and the developer, where, each segment is offset at 90 degrees to the succeeding segment, where, the end of the segment has edges that are cut parallel with the longitudinal axis to avoid a thinning of the wall and thereby strengthening the mixing spiral, and, where, the mixing spiral mixes the dye material and the developer.

31. The device of claim 18, where, the means for extruding the dye comprises a compression/injection device which comprises a rear compression end and an injector body, where the rear compression end consists of a cylindrical member with one closed end and one open end, where, by pushing down on the rear compression end, a user applies pressure to two piston axels, which drive two piston heads, which put pressure on two partitions, where one partition is filled with dye material and the other partition is filled with developer, thereby extruding both dye material and developer through two openings and two annular seals into a mixing channel in which is located a mixing spiral which mixes the dye material and the developer, a top which collects the mixture of dye material and developer and can be used to apply the mixture to hair.

32. The device of claim 18, where, the partitions are located with the developer partition enclosed in an inner cylinder inside of an outer cylinder in which the dye material is stored, where the outer side of the developer partition defines the inner side of the dye material partition.

33. The device of claim 18, where, the partitions are located with one partition adjacent and abutting the other partition, where the partitions are not located with one partition inside another partition.

* * * * *